United States Patent
Miller et al.

(10) Patent No.: US 8,439,946 B2
(45) Date of Patent: *May 14, 2013

(54) SUTURE ANCHOR HAVING A SUTURE ENGAGING STRUCTURE AND INSERTER ARRANGEMENT

(75) Inventors: M. Todd Miller, San Jose, CA (US);
Chad Wayne Lewis, Layton, UT (US);
David Eloy Quiñones Morales, Arroyo, PR (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/476,525

(22) Filed: May 21, 2012

(65) Prior Publication Data

US 2012/0232590 A1     Sep. 13, 2012

Related U.S. Application Data

(63) Continuation of application No. 12/380,891, filed on Mar. 4, 2009, now Pat. No. 8,197,511, which is a continuation-in-part of application No. 11/903,738, filed on Sep. 24, 2007.

(51) Int. Cl.
*A61B 17/04*     (2006.01)

(52) U.S. Cl.
USPC .......................................................... 606/232

(58) Field of Classification Search .................... 606/232
See application file for complete search history.

(56) References Cited

U.S. PATENT DOCUMENTS

| | | | |
|---|---|---|---|
| 146,023 A | 12/1873 | Russell |
| 197,933 A | 12/1877 | Harvey |
| 2,570,465 A | 10/1951 | Lundholm |
| 3,233,500 A | 2/1966 | DeVellier |
| 3,997,138 A | 12/1976 | Crock et al. |
| 4,175,555 A | 11/1979 | Herbert |
| 4,340,184 A | 7/1982 | Poss |
| 4,507,817 A | 4/1985 | Staffeld |
| 4,537,185 A | 8/1985 | Stednitz |
| 4,632,100 A | 12/1986 | Somers et al. |
| 4,640,271 A | 2/1987 | Lower |
| 4,738,255 A | 4/1988 | Goble et al. |
| 4,741,330 A | 5/1988 | Hayhurst |
| 4,854,311 A | 8/1989 | Steffee |
| 4,863,383 A | 9/1989 | Grafelmann |
| 4,870,957 A | 10/1989 | Goble et al. |
| 5,037,422 A | 8/1991 | Hayhurst et al. |
| 5,047,030 A | 9/1991 | Draenert |

(Continued)

FOREIGN PATENT DOCUMENTS

| AU | 0784963 B2 | 11/2002 |
|---|---|---|
| CA | 2 386 621 A1 | 11/2002 |

(Continued)

*Primary Examiner* — Melanie Tyson
(74) *Attorney, Agent, or Firm* — Flynn, Thiel, Boutell & Tanis, P.C.

(57) ABSTRACT

A suture anchor and inserter arrangement, including a suture anchor for implanting in hard tissue, such as bone, and an inserter device for installing the suture anchor in hard tissue. The suture anchor carries thereon a suture-engaging structure formed as a loop, which loop defines an attachment location for a working suture associated with the inserter device so as to attach the working suture to the suture anchor.

20 Claims, 13 Drawing Sheets

U.S. PATENT DOCUMENTS

| | | | |
|---|---|---|---|
| 5,100,417 A | 3/1992 | Cerier et al. |
| 5,156,616 A | 10/1992 | Meadows et al. |
| 5,224,946 A | 7/1993 | Hayhurst et al. |
| 5,258,016 A | 11/1993 | DiPoto et al. |
| 5,370,662 A | 12/1994 | Stone et al. |
| 5,417,533 A | 5/1995 | Lasner |
| 5,456,685 A | 10/1995 | Huebner |
| 5,472,452 A | 12/1995 | Trott |
| 5,549,633 A | 8/1996 | Evans et al. |
| 5,571,139 A | 11/1996 | Jenkins, Jr. |
| 5,573,548 A | 11/1996 | Nazre et al. |
| 5,584,836 A | 12/1996 | Ballintyn et al. |
| 5,601,557 A | 2/1997 | Hayhurst |
| 5,601,558 A | 2/1997 | Torrie et al. |
| 5,628,766 A | 5/1997 | Johnson |
| 5,643,320 A | 7/1997 | Lower et al. |
| 5,647,874 A | 7/1997 | Hayhurst |
| D385,352 S | 10/1997 | Bales et al. |
| 5,690,676 A | 11/1997 | DiPoto et al. |
| 5,709,708 A | 1/1998 | Thal |
| 5,725,529 A | 3/1998 | Nicholson et al. |
| 5,733,307 A | 3/1998 | Dinsdale |
| 5,814,070 A | 9/1998 | Borzone et al. |
| 5,871,486 A | 2/1999 | Huebner et al. |
| 5,891,146 A | 4/1999 | Simon et al. |
| 5,891,168 A | 4/1999 | Thal |
| 5,893,880 A | 4/1999 | Egan et al. |
| 5,911,721 A | 6/1999 | Nicholson et al. |
| 5,941,882 A | 8/1999 | Jammet et al. |
| 5,951,560 A | 9/1999 | Simon et al. |
| 5,957,953 A | 9/1999 | DiPoto et al. |
| 5,964,764 A | 10/1999 | West, Jr. et al. |
| 5,964,768 A | 10/1999 | Huebner |
| 5,964,783 A | 10/1999 | Grafton et al. |
| 6,030,162 A | 2/2000 | Huebner |
| 6,079,921 A | 6/2000 | Gauthier et al. |
| 6,096,060 A | 8/2000 | Fitts et al. |
| 6,117,162 A | 9/2000 | Schmieding et al. |
| 6,139,565 A | 10/2000 | Stone et al. |
| 6,214,031 B1 | 4/2001 | Schmieding et al. |
| 6,264,677 B1 | 7/2001 | Simon et al. |
| 6,299,615 B1 | 10/2001 | Huebner |
| 6,436,124 B1 | 8/2002 | Anderson et al. |
| 6,468,277 B1 | 10/2002 | Justin et al. |
| 6,511,499 B2 | 1/2003 | Schmieding et al. |
| 6,517,564 B1 | 2/2003 | Grafton et al. |
| 6,517,578 B2 | 2/2003 | Hein |
| 6,569,188 B2 | 5/2003 | Grafton et al. |
| 6,610,080 B2 | 8/2003 | Morgan |
| 6,616,665 B2 | 9/2003 | Grafton et al. |
| 6,635,074 B2 | 10/2003 | Bartlett |
| 6,641,597 B2 | 11/2003 | Dreyfuss et al. |
| 6,648,892 B2 | 11/2003 | Martello |
| 6,652,563 B2 | 11/2003 | Dreyfuss |
| 6,685,728 B2 | 2/2004 | Sinnott et al. |
| 6,726,707 B2 | 4/2004 | Pedlick et al. |
| 6,730,092 B2 | 5/2004 | Songer |
| 6,773,436 B2 | 8/2004 | Donnelly et al. |
| 6,840,953 B2 | 1/2005 | Martinek |
| 6,887,259 B2 | 5/2005 | Lizardi |
| 6,916,333 B2 | 7/2005 | Schmieding et al. |
| 6,923,824 B2 | 8/2005 | Morgan et al. |
| 7,081,126 B2 | 7/2006 | McDevitt et al. |
| 7,090,675 B2 | 8/2006 | Songer |
| 7,163,540 B2 | 1/2007 | Martello |
| 7,189,251 B2 | 3/2007 | Kay |
| 7,195,634 B2 | 3/2007 | Schmieding et al. |
| 7,217,279 B2 | 5/2007 | Reese |
| 7,226,469 B2 | 6/2007 | Benavitz et al. |
| 7,232,455 B2 | 6/2007 | Pedlick et al. |
| 7,309,337 B2 | 12/2007 | Colleran |
| 7,322,978 B2 | 1/2008 | West, Jr. |
| 7,500,983 B1 | 3/2009 | Kaiser et al. |
| 7,530,990 B2 | 5/2009 | Perriello et al. |
| 7,588,587 B2 | 9/2009 | Barbieri et al. |
| 7,611,521 B2 | 11/2009 | Lubbers et al. |
| 7,678,134 B2 | 3/2010 | Schmieding et al. |
| 7,695,495 B2 | 4/2010 | Dreyfuss |
| 7,780,701 B1 | 8/2010 | Meridew et al. |
| 7,828,820 B2 | 11/2010 | Stone et al. |
| 7,846,180 B2 | 12/2010 | Cerier |
| 7,862,585 B2 | 1/2011 | Li et al. |
| 7,883,528 B2 | 2/2011 | Grafton et al. |
| 7,883,529 B2 | 2/2011 | Sinnott et al. |
| 7,909,851 B2 * | 3/2011 | Stone et al. ............ 606/232 |
| 8,029,536 B2 | 10/2011 | Sorensen et al. |
| 8,114,127 B2 | 2/2012 | West, Jr. |
| 8,114,128 B2 | 2/2012 | Cauldwell et al. |
| 8,197,511 B2 * | 6/2012 | Miller et al. ............ 606/232 |
| 2002/0173822 A1 | 11/2002 | Justin et al. |
| 2003/0171778 A1 | 9/2003 | Lizardi |
| 2004/0093030 A1 | 5/2004 | Cox et al. |
| 2004/0106950 A1 | 6/2004 | Grafton et al. |
| 2004/0153103 A1 | 8/2004 | Schwartz et al. |
| 2004/0167576 A1 | 8/2004 | Pedlick et al. |
| 2004/0172062 A1 | 9/2004 | Burkhart |
| 2004/0254580 A1 | 12/2004 | Boock et al. |
| 2005/0075636 A1 | 4/2005 | Gotzen |
| 2005/0222618 A1 | 10/2005 | Dreyfuss et al. |
| 2005/0222619 A1 | 10/2005 | Dreyfuss et al. |
| 2005/0245932 A1 | 11/2005 | Fanton et al. |
| 2005/0267479 A1 | 12/2005 | Morgan et al. |
| 2006/0161159 A1 | 7/2006 | Dreyfuss et al. |
| 2006/0189993 A1 | 8/2006 | Stone |
| 2006/0190042 A1 | 8/2006 | Stone et al. |
| 2006/0293675 A1 | 12/2006 | Li et al. |
| 2007/0005069 A1 | 1/2007 | Contiliano et al. |
| 2007/0032792 A1 | 2/2007 | Collin et al. |
| 2007/0060922 A1 | 3/2007 | Dreyfuss |
| 2007/0073299 A1 | 3/2007 | Dreyfuss et al. |
| 2007/0142836 A1 | 6/2007 | Schmieding et al. |
| 2007/0142837 A1 | 6/2007 | Dreyfuss |
| 2007/0173845 A1 | 7/2007 | Kim |
| 2007/0185494 A1 | 8/2007 | Reese |
| 2007/0219557 A1 | 9/2007 | Bourque et al. |
| 2007/0219558 A1 | 9/2007 | Deutsch |
| 2008/0009904 A1 | 1/2008 | Bourque et al. |
| 2008/0167660 A1 | 7/2008 | Moreau et al. |
| 2008/0306510 A1 | 12/2008 | Stchur |
| 2009/0082807 A1 | 3/2009 | Miller et al. |
| 2009/0234387 A1 | 9/2009 | Miller et al. |
| 2010/0094355 A1 | 4/2010 | Trenhaile |
| 2010/0100127 A1 | 4/2010 | Trenhaile |
| 2010/0152773 A1 | 6/2010 | Lunn et al. |
| 2011/0054526 A1 | 3/2011 | Stone et al. |
| 2011/0224727 A1 | 9/2011 | Housman et al. |

FOREIGN PATENT DOCUMENTS

| | | |
|---|---|---|
| EP | 1 260 182 A3 | 11/2002 |
| EP | 1 300 115 A1 | 4/2003 |
| EP | 1 486 171 A1 | 12/2004 |
| EP | 1 530 951 A2 | 5/2005 |
| EP | 1 762 187 A1 | 3/2007 |
| EP | 1 797 827 A1 | 6/2007 |
| FR | 2 254 298 | 11/1975 |
| FR | 02 588 332 | 4/1987 |
| JP | 2003010198 A1 | 1/2003 |
| SU | 01034734 | 8/1983 |

* cited by examiner

SUTURE ANCHOR HAVING A SUTURE ENGAGING STRUCTURE AND INSERTER ARRANGEMENT

CROSS-REFERENCE TO RELATED APPLICATIONS

This application is a continuation of U.S. patent application Ser. No. 12/380,891, filed Mar. 4, 2009 and issued on Jun. 12, 2012 as U.S. Pat. No. 8,197,511, which is a continuation-in-part application of co-pending U.S. patent application Ser. No. 11/903,738, filed Sep. 24, 2007.

FIELD OF THE INVENTION

This invention relates to a suture anchor and inserter arrangement for use in fixing surgical suture to hard tissue.

BACKGROUND OF THE INVENTION

During some injuries, soft tissue, such as tendons or ligaments, can tear away from hard tissue, such as bone. Accordingly, it becomes necessary to reattach the soft tissue to the bone in order to facilitate the healing process. Various types of devices are used to reattach tissue, such as screws, staples and suture anchors. The instant invention relates to this latter type of attachment device.

Suture anchors may be inserted into a preformed hole made in the hard tissue, while other anchors are self-tapping. The anchors typically include an eyelet or other structure through which lengths of repair suture or working suture are threaded, which working suture is inserted simultaneously with the anchor into the hard tissue. In this regard, in some anchors, the eyelet is disposed exteriorly on the anchor, for example adjacent to or even forming part of a drive head located on the proximal end of the anchor, and in other anchors is formed interiorly within a bore defined inside the anchor. The eyelet may be formed from suture material, as disclosed in U.S. Pat. No. 6,641,597, and in other instances is formed as a rigid and integral component of the anchor body, as disclosed in U.S. Pat. No. 5,584,836. A further suture-engaging structure is disclosed in U.S. Patent Publication No. 2005/0222618, wherein the anchor incorporates a rigid pin disposed transversely across an interior bore defined in the anchor. In this variation, the working sutures are inserted into the proximal end of the anchor bore and looped over the pin to secure the suture to the anchor.

It has also been discovered that increasing the biological integration of the suture anchor with the bone in which the anchor is implanted can reduce rejection potential and speed healing. One embodiment of a suture anchor according to the invention is hollow and includes a continuous through-bore, so that the tip or distal end of the anchor, which is embedded in the bone tissue, is open, allowing the permeation/migration of blood, bone marrow, and their components (including platelets and messenchymal stem cells) into the repair site. The anchor is further formed of a bio-absorbable material, which also enhances healing and integration of the suture and anchor into the bone tissue.

An inserter device or driver may be utilized in conjunction with the anchor to install or drive same into hard tissue and may carry working sutures thereon. For the purpose of providing pull-out resistance once the anchor is installed, some anchors are exteriorly threaded, while others are ribbed or barbed to provide appropriate pull-out resistance.

The suture anchor according to the present invention includes an anchor body having a distal end configured for insertion into hard tissue and a proximal end spaced from the distal end. The anchor body carries thereon a suture engagement structure which cooperates with working suture to attach same to the suture anchor. The suture-engaging structure may, according to one embodiment, be defined by suture material, and may be formed as a continuous loop of suture material having a portion thereof located interiorly of the anchor, such that the working suture is looped over this interior portion of the suture loop to engage the working suture with the anchor.

The suture anchor according to the invention in one embodiment is configured for cooperation with an inserter or driver device. The inserter device includes a handle for manipulating the device and an inserter shaft which supports the suture anchor at the distal end thereof. The inserter device carries working sutures, which working sutures are engaged with the anchor via the suture engagement structure as discussed above, and then extend proximally either interiorly or exteriorly of the inserter device.

One possible use of the arrangement is in arthroscopic shoulder surgery, wherein the dislocation of soft tissue relative to the bone is a fairly common injury. However, this arrangement may also be utilized for the repair of small joints, such as the elbow, wrist, ankle, hand or foot. The arrangement may additionally be used to reattach small ligaments in the knee.

Other objects and purposes of the invention will be apparent to persons familiar with arrangements of this general type upon reading the following specification and inspecting the accompanying drawings.

Figure 1:
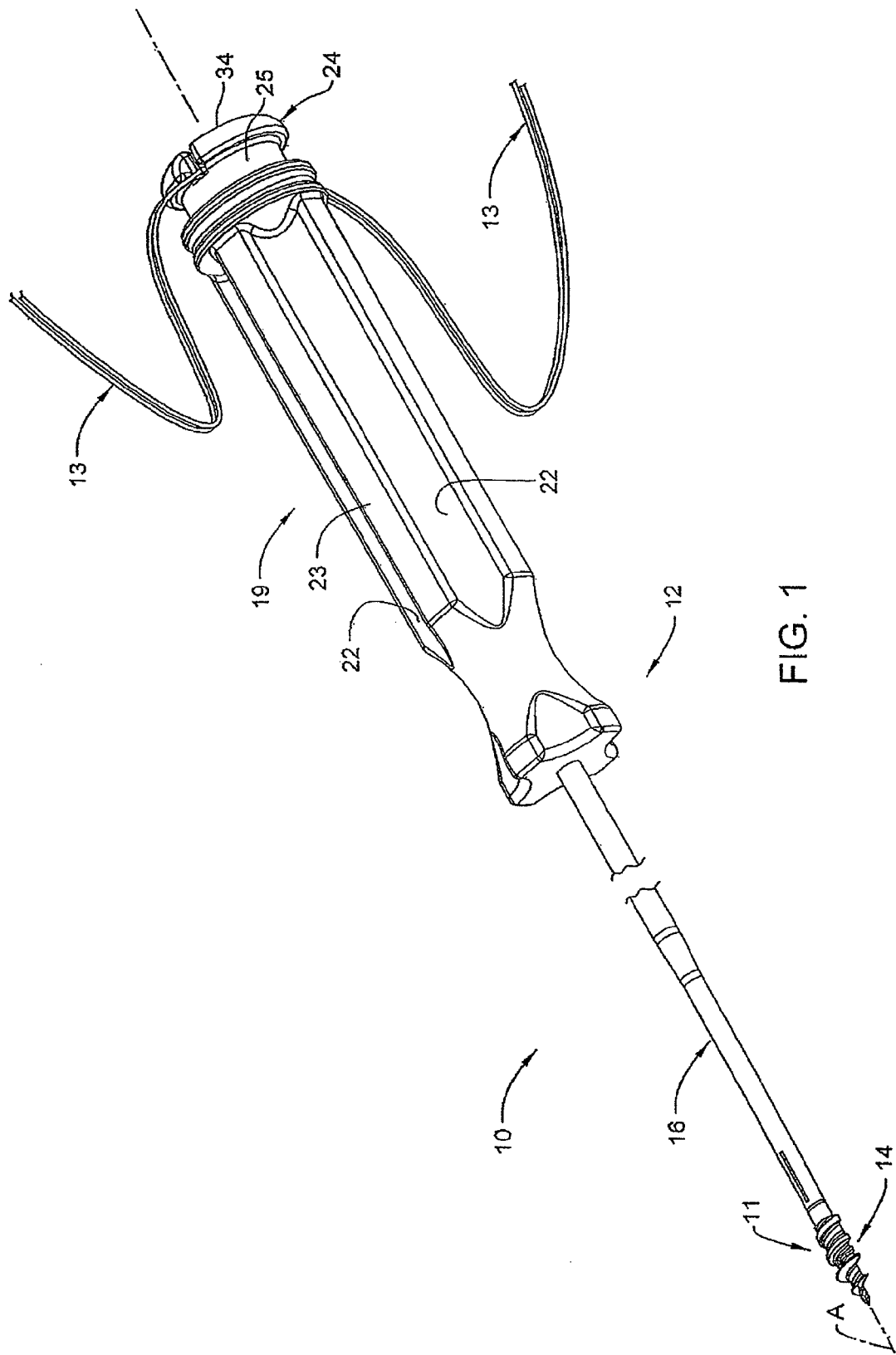
FIG. 1 is a fragmentary perspective view of the suture anchor and inserter arrangement according to the invention.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center and designated parts of thereof. The word "distally" will refer to the direction towards the end of the arrangement located closest to the patient, and the word "proximally" will refer to the direction towards the end of the arrangement located remote from the patient. Said terminology will include the words specifically mentioned, derivatives thereof, and words of similar import.

DETAILED DESCRIPTION

Figure 2:
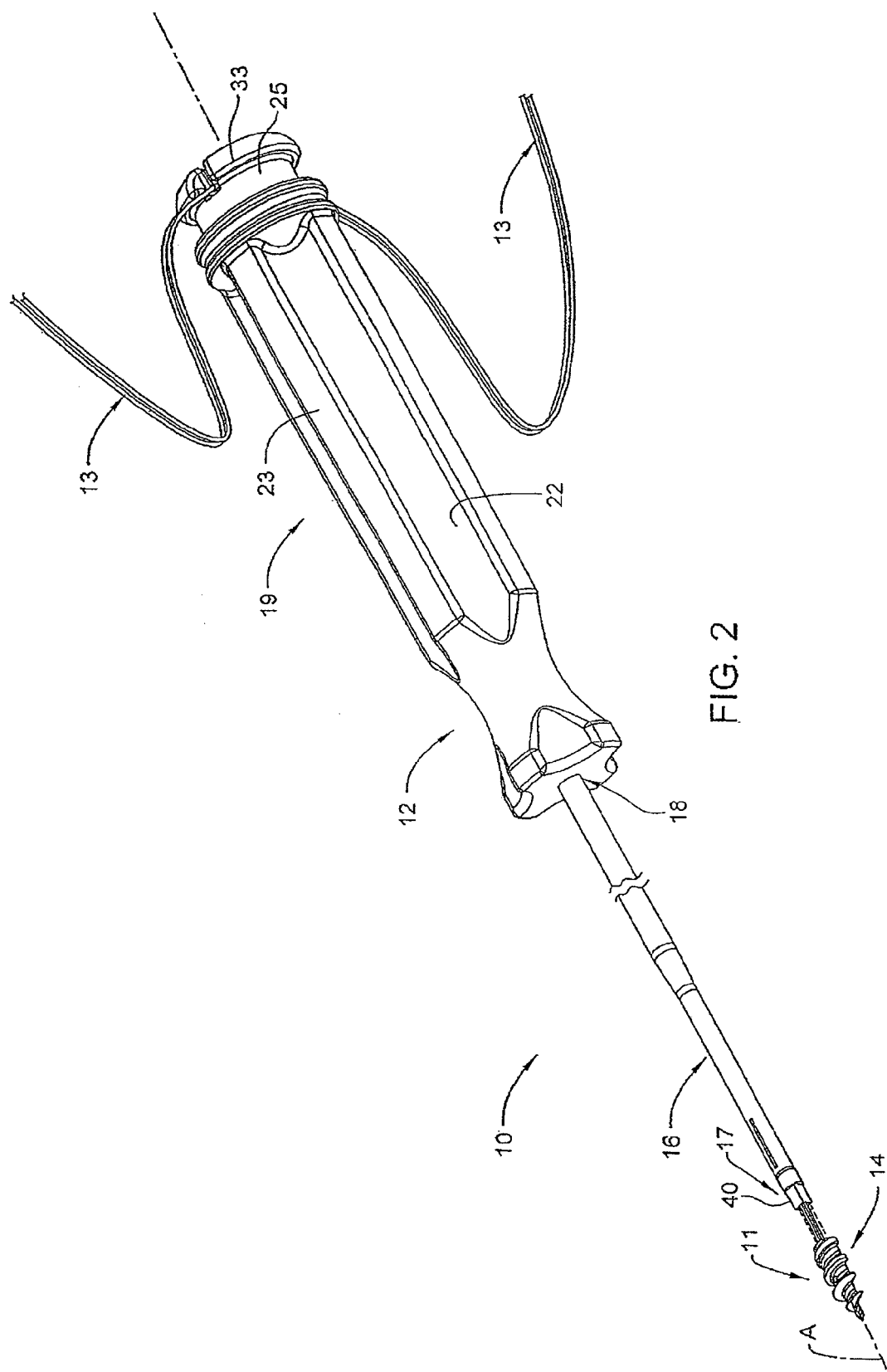
FIG. 2 is a fragmentary, partially-exploded perspective view of the arrangement of FIG. 1.

Referring to FIGS. 1 and 2, a suture anchor and inserter arrangement 10 is illustrated which is generally elongated in shape and defines a central longitudinal axis "A". The arrangement 10 generally includes a suture anchor 11 initially supported on an inserter device 12. Working sutures 13 extend through the inserter device 12 and cooperate with a suture-engaging structure 14 carried on the suture anchor 11, which suture-engaging structure 14 is fixed to the suture anchor 11 independently of any insert molding process.

Figure 5:
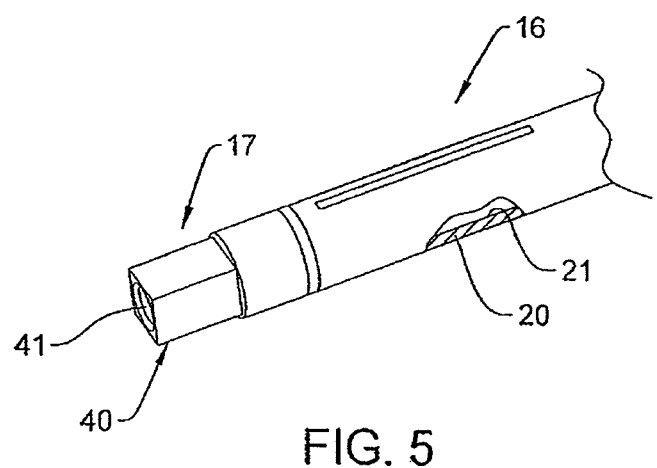
FIG. 5 is an enlarged, fragmentary perspective view of the distal end of the inserter device.
Figure 6:
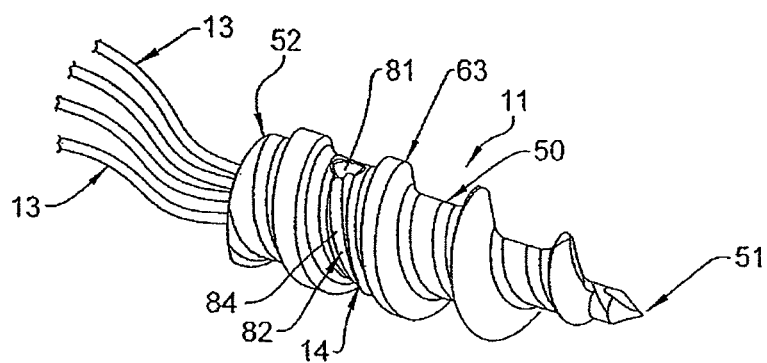
FIG. 6 is an enlarged perspective side view of the suture anchor with working sutures attached thereto.
Figure 7:
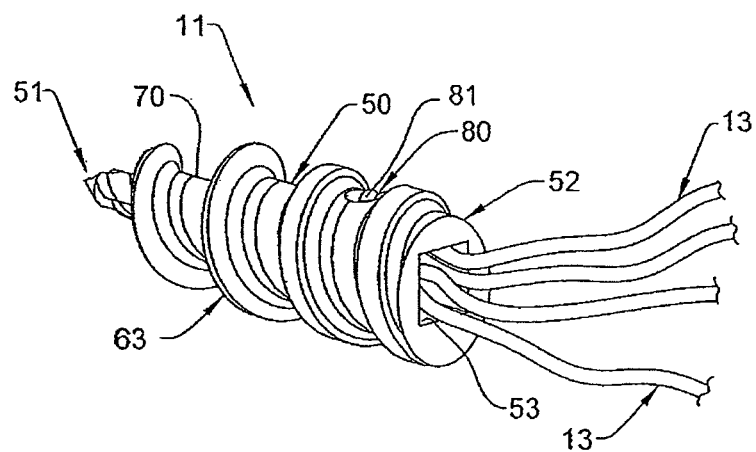
FIG. 7 is an enlarged perspective side view of the suture anchor rotated approximately 180° from the position shown in FIG. 6, showing the proximal end of the suture anchor.

The inserter device 12 is defined by an elongate and rigid inserter shaft 16 having a distal end 17 which engages the suture anchor 11, and a proximal end 18 fixed to a handle 19. Inserter shaft 16 includes a tubular sidewall 20 which defines a bore 21 extending throughout the longitudinal length of shaft 16 (FIG. 5). Handle 19 has an outer surface defining therein a series of axially or longitudinally extending recesses or depressions 22, wherein each circumferentially adjacent pair of recesses 22 are separated by a longitudinally extending projection 23. The alternating recesses 22 and projections 23 provide the handle 19 with a suitable gripping surface similar to a screwdriver for use when manipulating the arrangement 10 with the hand.

Figure 3:
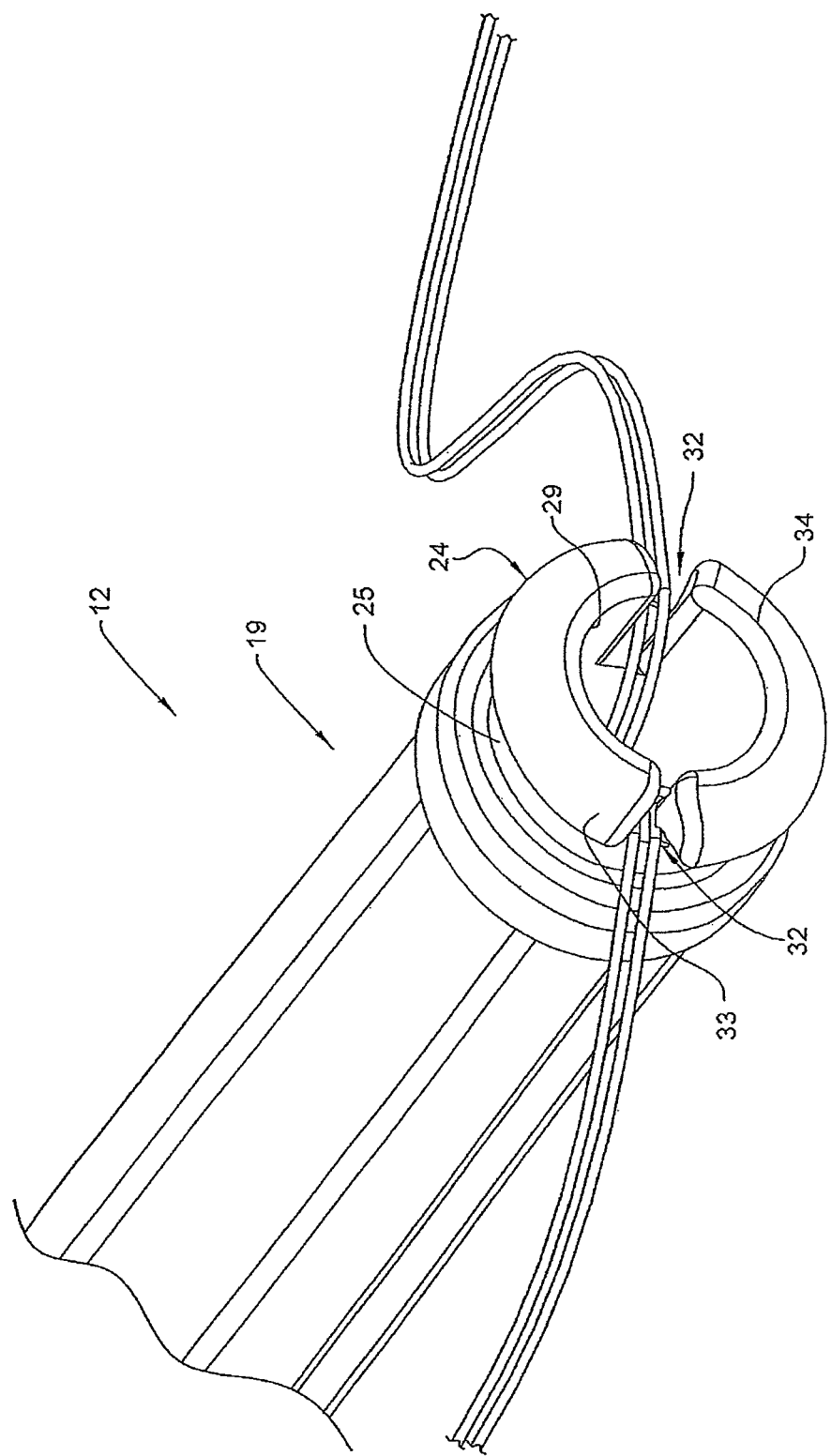
FIG. 3 is an enlarged, fragmentary perspective view of the proximal end of the inserter device.
Figure 4:
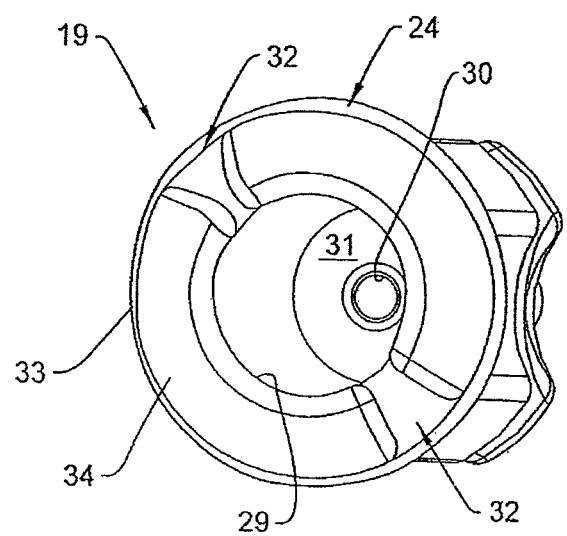
FIG. 4 is an enlarged perspective end view of the proximal end of the inserter device.

As best shown in FIGS. 3 and 4, handle 19 includes a generally annular flange 24 which defines the most proximal terminal end of handle 19. An annular recess 25 is located axially adjacent and distally of flange 24. Handle 19 defines therein a bore including a proximal bore portion 29 opening proximally or axially through flange 24, and a distal bore portion 30. Distal bore portion 30 is in communication with, and has a lesser diameter than, proximal bore portion 29 and extends distally therefrom throughout the longitudinal extent of handle 19 for communication with bore 21 of inserter shaft 20. Handle 19 additionally includes a transversely oriented wall 31 which defines the terminal distal extent of proximal bore portion 29, and through which wall 31 distal bore portion 30 opens for communication with proximal bore portion 29.

In the illustrated embodiment, a pair of slots 32 which cooperate with free ends of working sutures 13 are provided within the proximal end of handle 19 diametrically opposite one another. Slots 32 as shown are identical to one another, and only one of same will accordingly be described herein. Slot 32 opens sidewardly outwardly through an outermost side surface 33 of flange 24, axially through a terminal proximal end surface 34 of flange 24, and sidewardly inwardly for communication with proximal bore portion 29. Further, slot 32 extends distally a short distance from flange 24 so as to communicate with and open into annular recess 25 of handle 19.

With reference to FIG. 5, the distal end 17 of the inserter shaft 16 mounts thereon a projection 40. In the illustrated embodiment, projection 40 is polygonal in configuration so as to engage with the proximal end of the suture anchor 11. In one embodiment, the projection 40 has a rectangular cross-section. Projection 40 defines therein a centrally-located bore 41 which communicates with bore 21 of inserter shaft 16. It will be appreciated that other configurations of projection 40 are within the scope of the instant invention.

Turning now to suture anchor 11 as shown in FIGS. 6-10, same includes a generally elongate anchor body 50 defining a distal end 51 which is the end first inserted into the bone and a proximal end 52 associated with the distal end 17 of inserter shaft 16. A bore 53 centered on longitudinal axis A is defined within anchor body 50 and includes a distal portion 54 which terminates at an end face 55 and a proximal portion 56 which opens outwardly through the proximal end 52 of anchor 11. In the illustrated embodiment, proximal portion 56 of bore 53 is of a complementary polygonal profile as projection 40 of inserter device 12.

Figure 9:
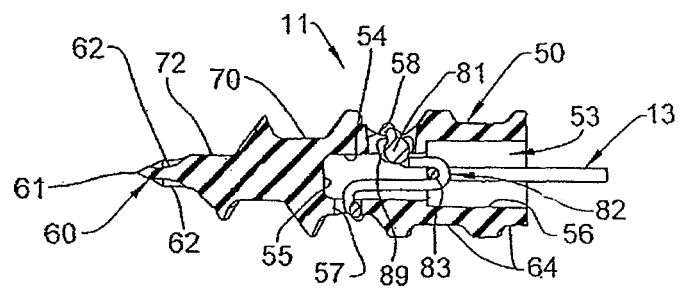
FIG. 9 is a cross-sectional view of the suture anchor, taken generally along line 9-9 in FIG. 8.
Figure 10:
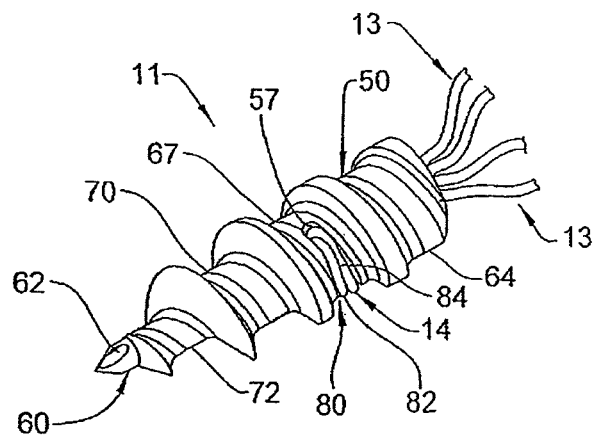
FIG. 10 is an enlarged perspective side view of the suture anchor.

With reference to FIG. 9, anchor body 50 additionally defines therein a pair of transversely oriented passages which communicate with central bore 53 and open outwardly through the outer surface of body 50. Specifically, a first passage 57 extends in a generally transverse or radial manner from a distal region of distal bore portion 54 and opens outwardly through outer surface of anchor body 50. A second passage 58 is disposed in axially and circumferentially-spaced relation from first passage 57. Passage 58, which is the larger of the two passages, extends generally radially or transversely from a proximal region of distal bore portion 54 and opens outwardly through the outer surface of body 50. In the illustrated embodiment, passages 57 and 58 are diametrically opposite one another (i.e. about 180° from one another) on anchor body 50. However, passages 57 and 58 may be located at greater or lesser circumferential distances from one another along anchor body 50.

Anchor body 50 terminates at the distal end 51 in a tip portion 60 which is conical in configuration and includes a point 61 which defines the most distal end of the anchor body 50. In one embodiment, a pair of flutes 62 are defined in tip portion 60 diametrically opposite one another, and serve as cutting edges and for clean-out purposes, as is conventional. Further, a continuous thread 63 wraps around anchor body 50, which starts at proximal end 52 and terminates just axially short of tip portion 60.

Figure 8:
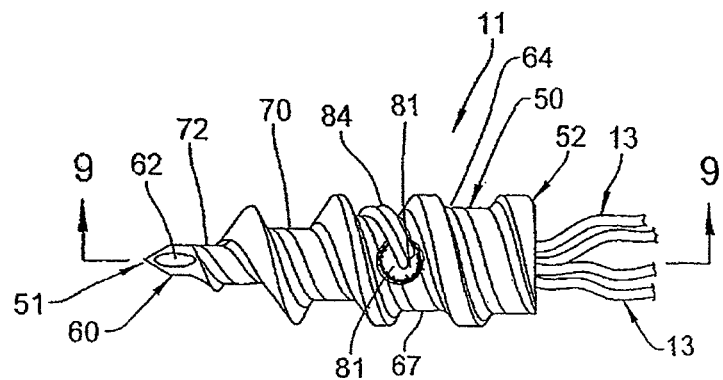
FIG. 8 is an enlarged plan view of the suture anchor.

With reference to FIGS. 8 and 9, anchor body 50 is of a cylindrically stepped configuration, and the outer diameter of such configuration steps downwardly or lessens in the direction from the proximal end 52 to the distal end 51. More specifically, this stepped configuration is defined by a first proximal and cylindrical stepped section 64 having the largest outer diameter of body 50. A second generally centrally located stepped section 67 is disposed axially adjacent stepped section 64, and is of a lesser diameter than section 64. A third generally centrally located and cylindrical stepped section 70 is disposed axially adjacent section 67 and is of a lesser diameter than section 67. A fourth distal and cylindrical stepped section 72 is located axially between section 70 and tip portion 60 and is of a lesser diameter than section 70. The tip portion 60 is located distally of section 70, and defines the portion of anchor body 50 having the smallest outer cylindrical diameter. Further, the thickness of thread 63 at the outer diameter thereof, starting at approximately midway along anchor body 50, increases as the thread 63 extends proximally.

FIGS. 6-10 illustrate the working sutures 13 attached to the suture anchor 11. In this regard, suture anchor 11 carries thereon the suture-engaging structure 14, which effectively serves as an attachment point for the working sutures 13. In the illustrated embodiment, the suture-engaging structure 14 is defined by suture material which is fixed to the anchor body 50. Specifically, a small length of suture material extends from distal portion 54 of central bore 53 outwardly through passage 57, across the exterior surface of anchor body 50, and then back into passage 58 and distal bore portion 54. The opposite free ends of the length of suture material are then tied together to form a knot 81, and this knot 81 may be located within passage 58 or alternatively within central bore 53. In one embodiment, adhesive 89 may be utilized to reinforce and further secure knot 81. In this regard, various types of biocompatible adhesives which may be utilized to secure knot 81 are cyanoacrylates, such as Histoacryl (an n-butyl cyanoacrylate distributed by TissueSeal LLC), ethyl cyanoacrylate, butyl cianoacrylate, and octyl cyanoacrylate. Polycaprolactone (PCL), Poly-L-lactide acid (PLLA), and polyglycolic acid (PGA) may also be utilized.

The suture material thus forms a closed loop 82 having an interior section 83 located interiorly of the anchor body 50 and an exterior section 84 located exteriorly of the anchor body 50. In this regard, exterior section 84 extends circumferentially about anchor body 50 between passages 57 and 58 within and along a portion of stepped section 67. The stepped section 67 of anchor body 50 located between two adjacent thread flights of thread 63 thus defines a sidewardly-opening and circumferentially extending groove 80. Groove 80 extends along an angle of at least about 90°, and in the illustrated embodiment extends along an angle of about 180°.

As best shown in FIG. 9, the free ends of working sutures 13 extend into the proximal end 52 of the anchor body 50 into central bore 53, loop around or over the interior section 83 of loop 82, and then extend proximally back out of the anchor body 50. Loop 82 thus defines a non-rigid or soft structure which is fixed to anchor body 50 and utilized to define an attachment point for the working suture 13.

Figure 15:
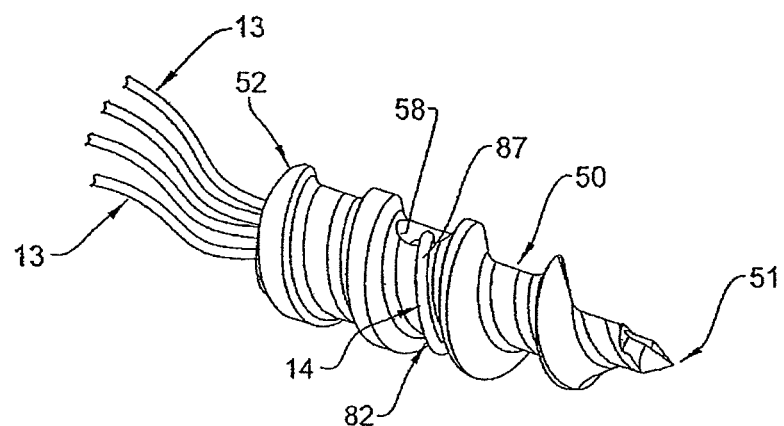
FIG. 15 is an enlarged perspective side view of the suture anchor with an alternative suture engagement structure.
Figure 16:
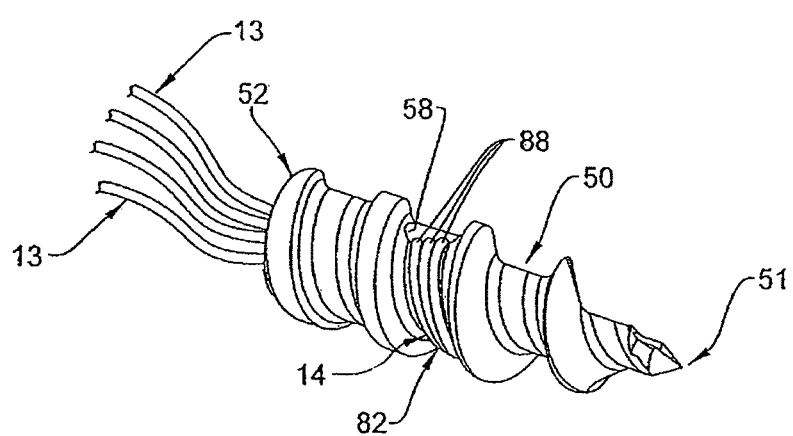
FIG. 16 is an enlarged perspective side view of the suture anchor with yet another alternative suture engagement structure.
Figure 17:
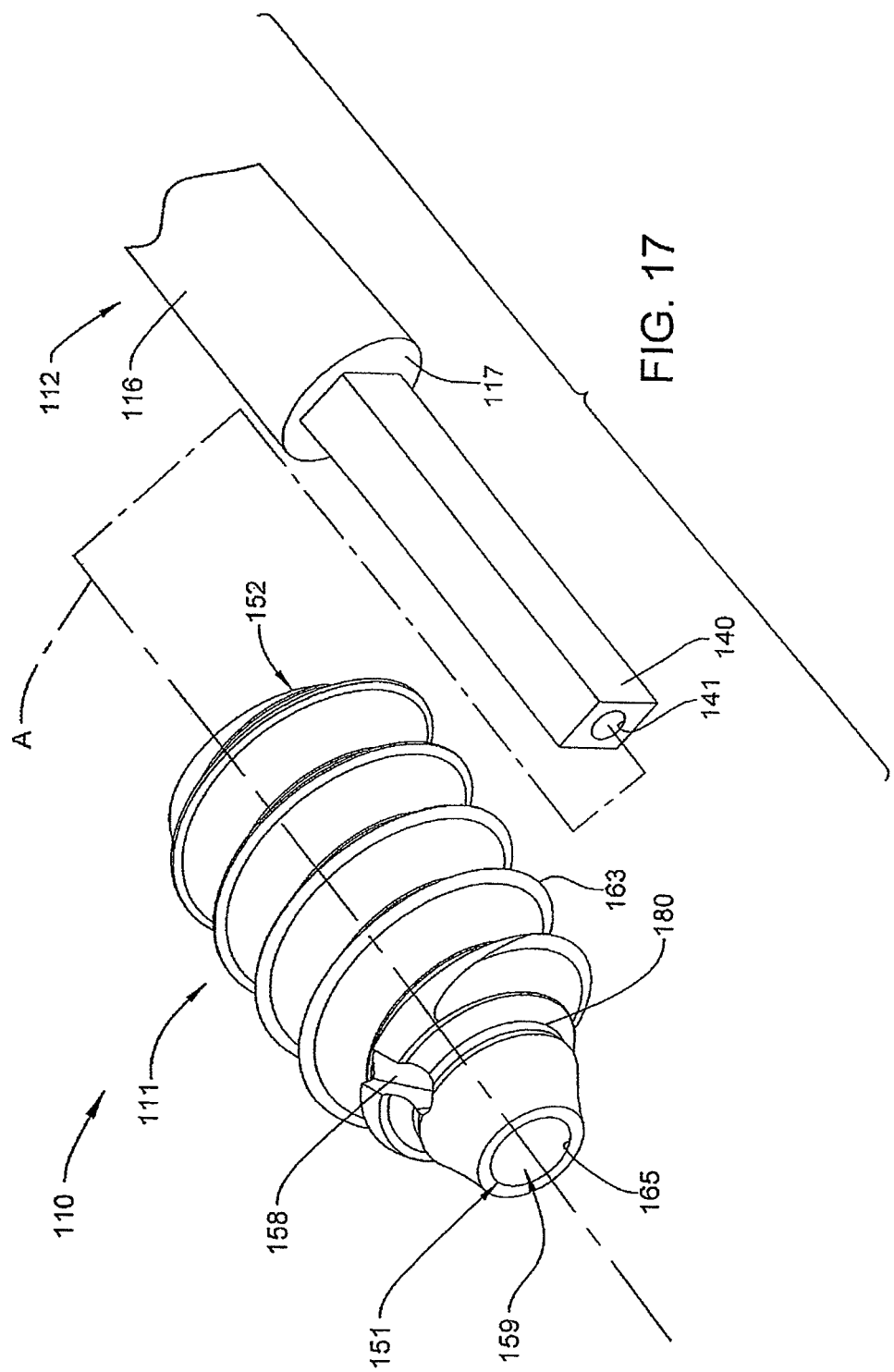
FIG. 17 is a fragmentary, partially exploded perspective view of a suture anchor and inserter arrangement according to a further embodiment of the invention.
Figure 18:
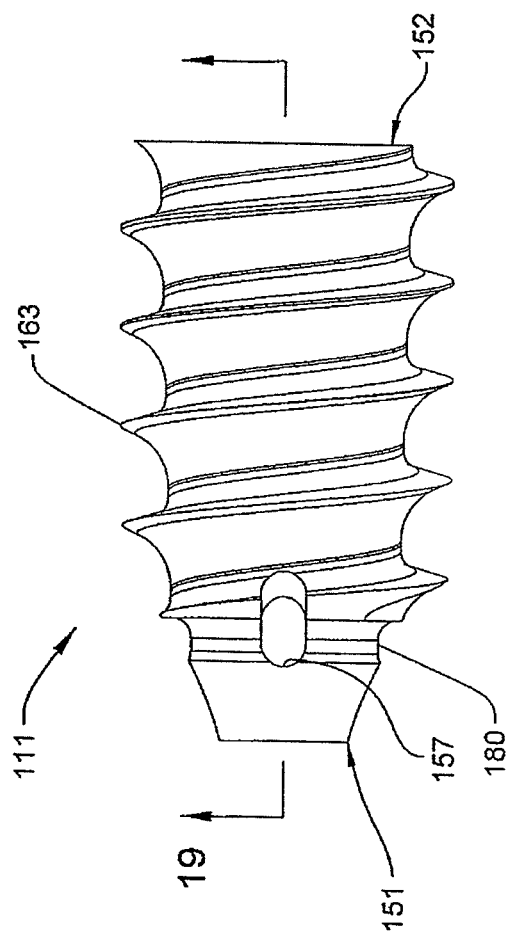
FIG. 18 is a plan view of the suture anchor of FIG. 17.
Figure 19:
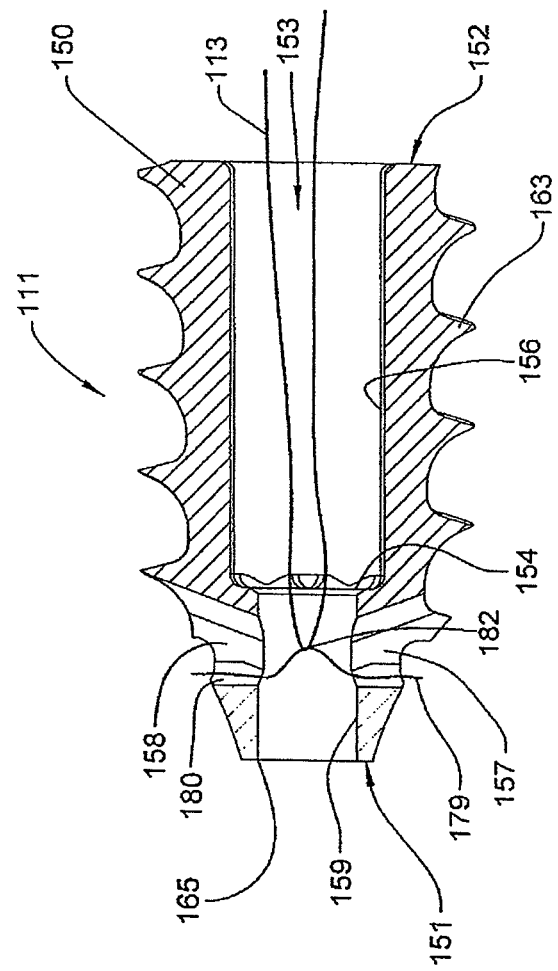
FIG. 19 is a cross-sectional view of the suture anchor, taken generally along line 19-19 of FIG. 18.

In the illustrated embodiment, two strands of suture define loop 82. However, it will be appreciated that suture loop may be defined by a single strand 87 of suture material as shown in the embodiment of FIG. 15, or triple strands 88 of suture material as shown in the embodiment of FIG. 16. In this regard, it may be desirable to use a single strand 87 of suture material to form loop 82 if such material has sufficient strength, so as to simplify assembly, minimize materials, and reduce the volume of suture material within anchor body 50. Also, it may be desirable to use triple strands 88 if the suture material utilized has a smaller diameter but is not of sufficient strength such that additional strands are necessary.

One method of assembling the suture anchor 11 onto the inserter device 12 is as follows. Free ends of two separate working or repair sutures 13 are inserted into the proximal end of inserter device 12 through proximal bore portion 29, into distal bore portion 30, through inserter shaft bore 21 and through bore 41 of projection 40. These free ends of the working sutures 13 are inserted into bore 53 at the proximal end of suture anchor 11, over the interior section 83 of suture loop 82 and then brought back out of the anchor bore 53 and back through the distal end 17 of inserter device 12 until same emerge at proximal bore portion 29 thereof. Alternatively, instead of utilizing two pairs of working sutures 13, a single working suture could be engaged with suture loop 82. Three or more working sutures could also be utilized.

The bore 53 which opens at the proximal end of anchor 11 is circumferentially or rotationally aligned with the projection 40 of inserter device 12 at the distal end of inserter shaft 16, and the projection 40 is inserted into the bore 53. The free ends of the working sutures 13 located adjacent handle 19 are then pulled in a proximal direction so as to tension the working sutures 13, and the working sutures 13 may then be pulled transversely or sidewardly relative to handle 19 to engage the working sutures 13 within one of the slots 32 so as to maintain the sutures 13 in a fixed position relative to inserter device 12. If desirable or necessary, for example for storage purposes, the free ends of working sutures 13 may be wrapped or coiled around handle 19 and stored within annular recess 25, and the free ends fixed in place within the opposite slot 32.

Figure 11:
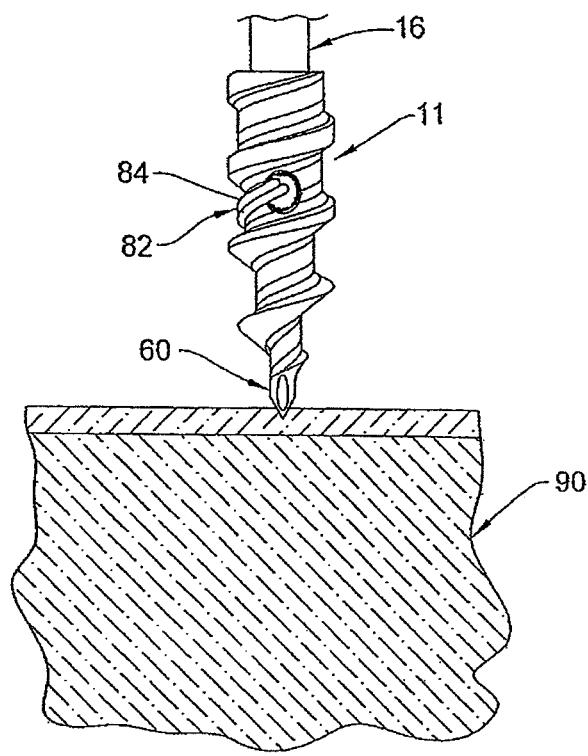
FIG. 11 is a fragmentary view illustrating the suture anchor being installed within a bone using the inserter device.
Figure 12:
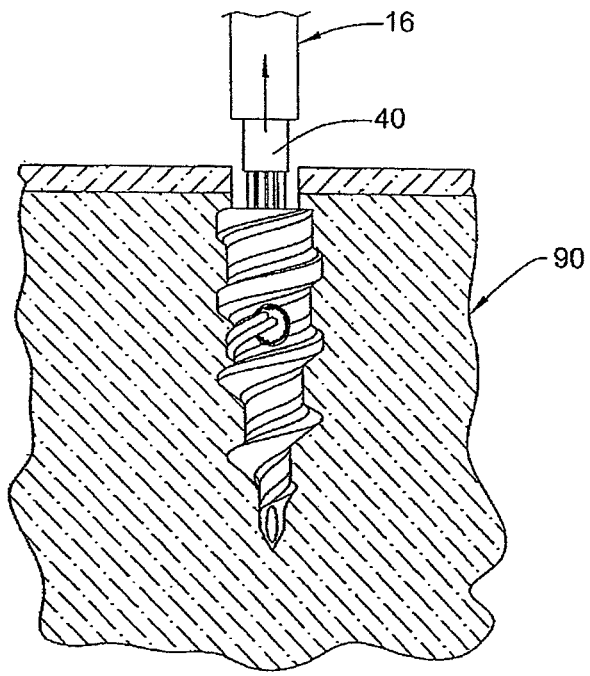
FIG. 12 is a fragmentary view illustrating the inserter device being pulled away from the suture anchor.

The suture anchor 11 is intended for implanting within hard tissue, such as bone 90. One method of implanting anchor 11 will be described with reference to FIGS. 11-14. In some implanting procedures, i.e. when the suture anchor 11 is constructed of a hard material such as titanium, the anchor 11 is self-tapping, and thus no hole need be pre-formed in the bone 90 to insert the anchor 11. With this type of anchor, with the suture anchor 11 installed on the inserter device 12 as discussed above, the tip portion 60 of the anchor 11 is placed in position relative to the bone 90 and the anchor 11 is rotatably driven into the bone 90 utilizing device 12 (FIG. 11). Once the anchor 11 is located at the desired depth within bone 90, the inserter device 12 is pulled in a proximal direction away from the anchor 11 (FIG. 12) to unseat the anchor 11 therefrom. In this regard, the working sutures 13 would be released from slot 32 of handle 19 prior to the aforementioned step, so as to allow working sutures 13 to move freely relative to the inserter device 12 as the anchor 11 is deployed therefrom. Continued movement of the inserter device 12 in a proximal direction frees the working sutures 13 from the device 12, so that the surgeon can use the sutures 13 to anchor soft tissue 92 to the bone 90.

Figure 13:
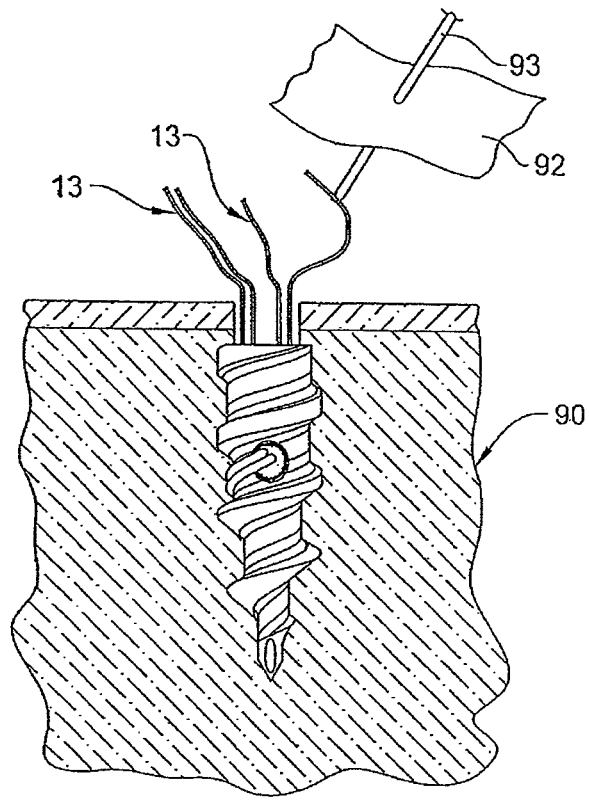
FIG. 13 is fragmentary view illustrating the attachment of the working sutures to soft tissue.
Figure 14:
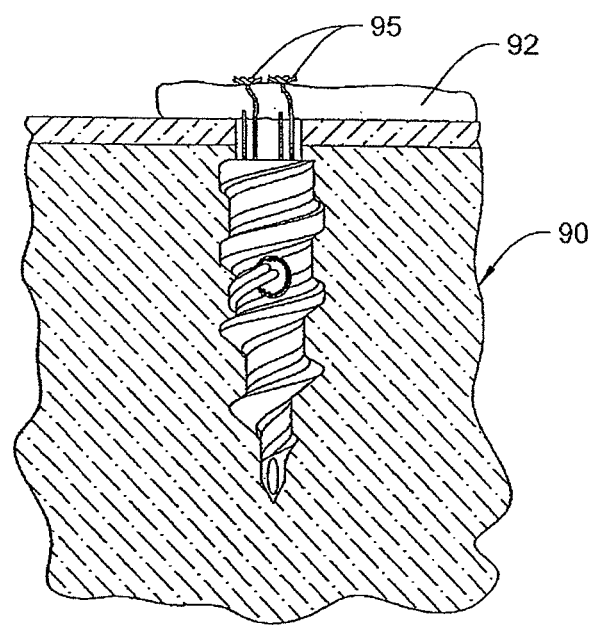
FIG. 14 is a fragmentary view illustrating the soft tissue fully attached to the bone.

As shown in FIG. 13, the surgeon utilizes a suitable surgical tool 93 to grasp one of the working sutures 13 and pull same through the soft tissue 92. The same step is performed with the opposite working suture 13. The two free ends of each of the working sutures 13 now extend around and through a portion of the soft tissue 92, and the surgeon forms sliding knots 95 in the working sutures 13. The knots 95 are moved down the working suture 13 to cinch the soft tissue 92 against the bone 90 at the location of anchor 11 (FIG. 14). Any excess length of each working suture 13 may then be removed, if necessary. Once the suture anchor 11 is seated within the bone 90, the stepped diameter of central body 50 of anchor 11 is believed to prevent improved resistant to proximal movement of the anchor 11 out of bone 90 so that the anchor 11 will remain firmly fixed therein. Further, the increasing thickness of thread 63 in the distal to proximal direction of the anchor as discussed above is also believed to provide improved pull-out resistance.

It will be appreciated that when the suture anchor 11 is constructed of softer materials, such as plastic, it is typically necessary to utilize a tap instrument to form a pre-formed hole in the bone 90. In this regard, the tap instrument has a pointed tip which initially punches through the bone 90, and has a threaded body located proximally of the pointed tip. The tap instrument is thus rotated relative to the bone so that a pre-formed threaded hole is defined in the bone 90. The tip portion 60 of the anchor 11 is then aligned with this hole, and the anchor 11 is rotatably driven into the bone 90.

The arrangement as discussed above includes the projection 40 on the distal end 17 of inserter device 12 which cooperates with the proximally-opening bore 53 of the suture anchor 11. It will be appreciated that this configuration could be reversed, for example, the suture anchor 11 could include a projection or external drive head which engages within a corresponding recess formed in the distal end of the inserter device 12. However, forming the anchor 11 with an internal construction for allowing cooperation with the inserter device 12 is believed advantageous as compared to conventional anchors which include externally projecting drive heads at their proximal ends. In this regard, configuring the anchor in this manner allows same to be made smaller, so as to cause less trauma to the patient, and also allows the anchor to be provided with a greater thread length within the available anchor length, and thus is believed to result in a better engagement of the anchor within the bone.

In addition, the cylindrically stepped configuration of the anchor body which decreases from the proximal end of the anchor towards the distal end is believed to provide improved pull-out resistance, as compared to conventional anchors having anchor bodies with a linearly tapered configuration.

The suture anchor 11 according to the invention may be constructed of any suitable rigid material, such as plastic or metal, and also may be constructed of bio-absorbable material or non-absorbable material. In this regard, one example of nonabsorbable plastic which may be utilized is PEEK, and one example of nonabsorbable metal which may be utilized is titanium. One example of an absorbable plastic which may be utilized is PLLA. Composite materials may also be used for both bio-absorbable and non-absorbable applications, such as PLLA/HA, which is a type of ceramic. It will be appreciated that other types of materials may be utilized in accordance with the invention, and the above are presented only as examples.

Additionally, the suture anchor 11 may have a length dimension of about 17 mm, and may have an outside diameter of about 5.5 mm or 6.5 mm. These dimensions are presented only as an example of relative dimensions of anchor 11, and are not to be limiting.

Referring now to FIGS. 17-20, a further embodiment of the suture anchor and inserter arrangement 110 is illustrated. The arrangement 110 includes a suture anchor 111 and an inserter device 112. Components which are similar or identical to components described above in previous embodiments are provided with the same reference number, plus 100.

The inserter device 112 includes a projection 140 at a distal end 117 thereof. The shaft 116 and projection 140 of the inserter device 112 include a centrally located bore 141 through which working sutures 113 are passed, as described above. A single working suture 113 is illustrated for clarity, but multiple working sutures can be used and are within the scope of the invention. In the alternative, suture anchor arrangements are known which integrate a suture/needle combination. The common curved needle configuration precludes passage of the suture through a cannulated inserter device 112. Therefore, a non-cannulated inserter or a partially cannulated inserter (not shown) in such an application would be compatible for use with the suture anchor 111, with the working suture 113 passing on the exterior surface of the inserter device.

In the illustrated embodiment, the suture anchor 111 has a body 150 formed of a bio-absorbable material, such as PLLA, discussed above. The body 150 includes a distal end 151 and a proximal end 152 through both of which ends 151, 152 a central bore 153 opens. Anchor body 150 additionally includes externally formed double-helix threads 163 running the length thereof and having a generally uniform thread diameter. The distal end 151 of the anchor body 150 tapers inwardly in the proximal to distal direction, and includes a central opening 165 which communicates with or is contiguous with the central bore 153. The threads can also be formed as a single helix (not shown) and fall within the scope of the invention.

The central bore 153 has a first or proximal bore portion 156 which extends from the proximal end 152 of the anchor body 150 to a distal end 154 located just proximate of the distal end 151, and a second or distal bore portion 159 which extends axially from distal end 151 to distal end 154 of bore portion 156, and has a lesser diameter than bore portion 156. Further, bore portion 156 has a cross-sectional profile which matches the external configuration of the projection 140 of the inserter device 112. The projection 140 is likewise configured for full-length insertion into bore portion 156 of bore 153 of the suture anchor body 150, and in the illustrated embodiment has a square profile. The projection 140 can also have other profiles, such as hexagonal, oval, or star-shaped, and remain within the scope of the invention.

A pair of passages 157, 158 extend transversely relative to the longitudinal axis A of the anchor 111, from within the bore portion 159 of the central bore 153 to the exterior of the anchor body 150. The passages 157, 158 open outwardly into a circumferential groove 180 defined in the exterior surface of the anchor body 150, which groove 180 extends around the entire circumference thereof.

Figure 20A:
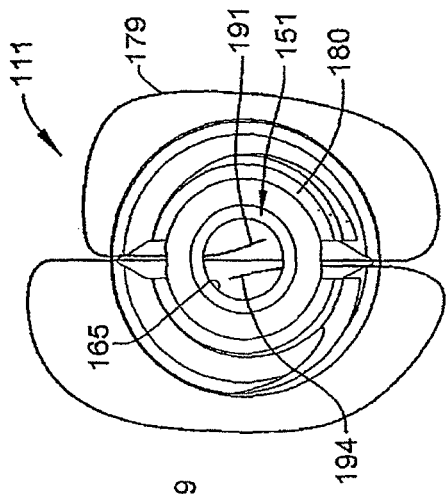
FIGS. 20A-20E are distal end views of the suture anchor of FIGS. 17-19, showing assembly of the soft eyelet to the anchor body.
Figure 20B:
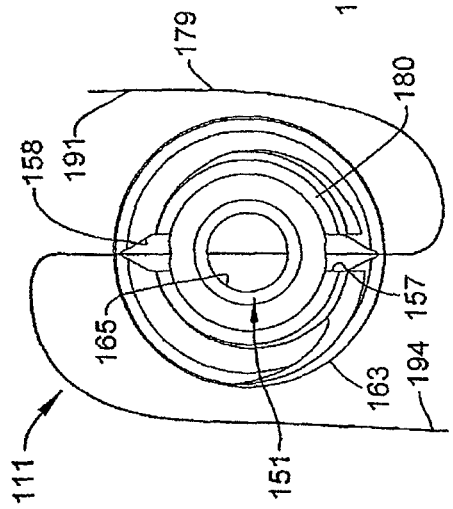
Figure 20C:
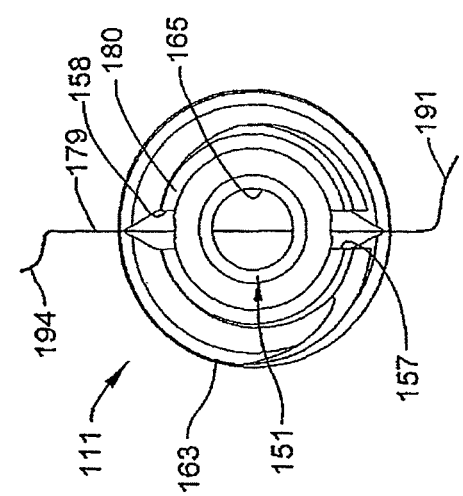
Figure 20D:
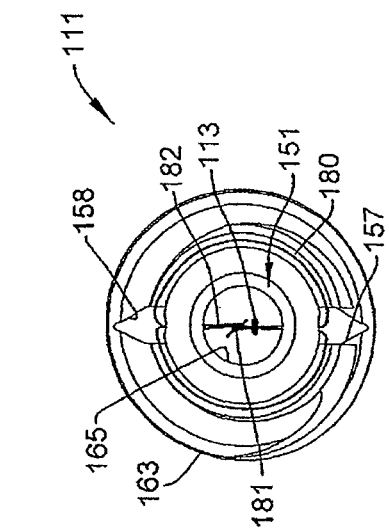
Figure 20E:
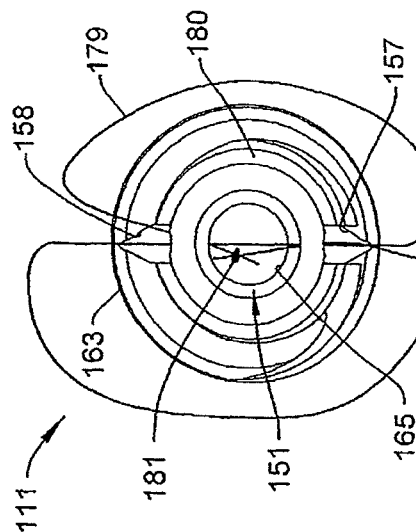

In order to form a soft eyelet for engaging the working sutures 113, a single strand of suture material 179 is passed through passages 157, 158 so that it extends through bore portion 159 and transversely to the longitudinal axis A of the anchor body 150, as shown in FIG. 20A. Each end 194, 191 of the suture material 179 is drawn 180° around the body 150 in the circumferential groove 180 (FIG. 20B) and inserted through the respective opposite passage 157, 158 back into bore portion 159 (FIG. 20C). The ends 194, 191 are then drawn outwardly through the opening 165 in the distal end 151 of the anchor body 150 and secured to one another, such as by a knot 181 (FIG. 20D), or as described above. The working suture 113 is loaded into inserter device 112 as discussed above, and the free end is drawn out from bore 141. The free end of working suture 113 is then drawn through the central bore 153 of the suture anchor 111 through distal end 154 to capture at least one of the two "passes" of the suture material 179 (FIG. 20E), which now form a loop 182. As tension is placed on the loop 182 by the working suture 113, the knot 181 is drawn into the opening 165, and the loop 182 is drawn into proximal bore portion 156 of the central bore 153. The free end of the working suture 113 is then drawn back through the central bore 141 of the inserter device 112.

The projection 140 is inserted into the proximal bore portion 156 of central bore 153 of the suture anchor 111 until the projection 140 extends the full depth of the bore portion 156 to distal end 154. The projection 140 thereby fully supports the length of the suture anchor 111, and increases the bearing surface between the projection 140 and the central bore 153 of the suture anchor 111. A given force is necessary to drive the suture anchor 111 into bone. The increased bearing surface between the projection 140 and the suture anchor 111 distributes this force over a greater area, thereby diminishing the shearing force exerted on the material of the anchor body 150. The projection 140 further provides full length support of the hollow suture anchor 111 to prevent its collapse during insertion into a pre-tapped hole in the bone. In the illustrated embodiment, the anchor 111 is not self-tapping and is provided with tapered distal end 151, and thus requires a pilot hole be prepared in the bone before insertion.

The anchor 111 is implanted in bone in a manner similar to that described above.

Although particular preferred embodiments have been disclosed in detail for illustrative purposes, it will be recognized that variations or modifications of the disclosed apparatus, including the rearrangement of parts, lie within the scope of the present invention.

What is claimed is:

1. A suture anchor arrangement comprising a suture anchor, said suture anchor including an anchor body having a longitudinal axis, a distal end configured for implanting into hard tissue and a proximal end spaced from said distal end, said anchor body defining therein a continuous bore extending from said proximal end to said distal end and opening axially through said distal end, a pair of passages each opening into said bore and communicating therewith, and a length of working suture for securing soft tissue to said anchor body, said anchor body including a suture-retention interface defining an attachment location on said anchor body for attachment of said working suture to said suture anchor, said interface including a loop having a first part extending from one said passage to the other said passage entirely within said bore, said first part of said loop defining said attachment location which is disposed entirely within said bore, said working suture being attached to said first part of said loop within said bore to interconnect soft tissue to said anchor body when said anchor body is installed within hard tissue, and said loop having a second part extending between said passages outside said bore, said second part of said loop extending along an exterior of said anchor body in a circumferential direction about the axis and between said passages.

2. The suture anchor arrangement of claim 1, wherein said loop is formed from suture material, and said loop has a pair of terminal free ends which are secured to one another such that said loop comprises a closed and continuous loop of said suture material fixed to said anchor body.

3. The suture anchor arrangement of claim 2, wherein said terminal free ends of said loop are tied to one another to form a knot, said knot being disposed within said bore proximate said distal end.

4. The suture anchor arrangement of claim 1, wherein said bore extends in a direction generally parallel with the longitudinal axis of said anchor body, and said passages are oriented transversely relative to said bore.

5. The suture anchor arrangement of claim 4, wherein said anchor body has a threaded exterior surface for engagement within a cavity defined in bodily tissue, and said bore defines a recess configured for engagement with an inserter device for facilitating insertion of said suture anchor into tissue, said recess opening proximally through said proximal end of said anchor body and extending from said proximal end substantially to said passages.

6. The suture anchor arrangement of claim 1, wherein said anchor body has an exterior surface and each said passage opens outwardly through said exterior surface through an outer end, said outer ends being radially aligned with one another along a line which extends through the longitudinal axis.

7. The suture anchor arrangement of claim 1, wherein said interface comprises a closed and continuous loop of suture material which is fixed to said anchor body independently of any insert molding process.

8. The suture anchor arrangement of claim 1, wherein said exterior of said anchor body includes an outer surface defining a circumferential groove therein in which said second part of said loop is disposed.

9. The suture anchor arrangement of claim 8, wherein said passages extend transversely to the longitudinal axis so as to open inwardly into said bore and outwardly into said groove, said second part of said loop occupying a portion of said groove.

10. The suture anchor arrangement of claim 9, wherein said loop has a third part extending along said exterior of said anchor body and occupying a further portion of said groove on an opposite side of said anchor body from said second part.

11. A suture anchor arrangement comprising:

a suture anchor including an anchor body defining a longitudinal axis, said anchor body having a distal end configured for insertion into hard tissue and a proximal end spaced axially from said distal end, said anchor body defining therein a substantially axially-extending bore disposed within an interior of said anchor body, and a pair of passages extending through said anchor body each in a direction transverse to the axis, each said passage having an inner end which opens into said bore and communicates therewith and an outer end spaced radially from the respective said inner end and opening through an exterior of said anchor body, said outer ends of the respective said passages being axially aligned with one another and spaced circumferentially from one another along said exterior of said anchor body;

a length of working suture for securing soft tissue to said anchor body; and a loop for securing said working suture to said anchor body, said loop having an interior portion disposed within said bore and extending between the respective said inner ends of said passages, said interior portion defining an attachment location for securing said working suture to said anchor body, said loop having an exterior portion extending circumferentially along said exterior of said anchor body between the respective said outer ends of said passages, said working suture being attached to said interior portion of said loop within said bore to interconnect soft tissue to said anchor body when said anchor body is installed within hard tissue.

12. The suture anchor arrangement of claim 11, wherein said exterior portion of said loop is a first exterior portion and said loop includes a second exterior portion extending circumferentially along said exterior of said anchor body between the respective said outer ends of said passages, said first and second exterior portions extending along opposite sides of said exterior of said anchor body.

13. The suture anchor arrangement of claim 11, wherein said loop comprises a closed, continuous and circular loop of suture material fixed to said anchor body and carried entirely on said anchor body so as not to extend axially beyond said proximal end thereof.

14. The suture anchor arrangement of claim 11, wherein said loop comprises a closed and continuous loop of suture material distinct from said working suture and having a pair of terminal free ends secured to one another so as to form said closed and continuous loop.

15. A suture anchor arrangement comprising:

a suture anchor including an anchor body defining a longitudinal axis, said anchor body having a distal end configured for insertion into hard tissue and a proximal end spaced axially from said distal end, said anchor body having a generally hollow interior and an exterior surface spaced radially outwardly from said hollow interior; and an attachment structure fixed to said anchor body, said attachment structure including a closed and continuous loop having an interior portion disposed entirely within said hollow interior of said anchor body and first and second loop portions, each of said first and second loop portions having an exterior portion disposed outside of said hollow interior and extending circumferentially along said exterior surface of said anchor body, said first and second loop portions extending along said exterior surface in opposite directions from one another, said interior portion extending transversely across and entirely within said hollow interior to define an attachment location disposed entirely within said hollow interior for securing a working suture to said anchor body.

16. The suture anchor arrangement of claim 15, wherein said attachment location is disposed adjacent said distal end of said anchor body, and said loop comprises a length of suture material having a pair of free terminal ends which are secured to one another such that said loop is a closed and continuous loop of suture material fixed to said anchor body and carried entirely on said anchor body so as not to extend axially beyond said proximal end thereof.

17. The suture anchor arrangement of claim 16, wherein each of said exterior portions of said first and second loop portions extend circumferentially about the axis in opposite directions from one another and along diametrically opposite sides of said exterior surface of said anchor body.

18. The suture anchor arrangement of claim 16, wherein said anchor body defines therein a pair of passages extending through said anchor body adjacent said distal end thereof and being oriented transversely relative to the axis, each said passage having an outer end which opens outwardly through said exterior surface of said anchor body and an inner end which opens inwardly into said hollow interior, said first and second loop portions extending through said passages such that said exterior portions thereof extend outwardly and out of said hollow interior through said outer ends of said passages, said exterior portions of said first and second loop portions extending circumferentially about the axis in opposite directions from one another and along diametrically opposite sides of said exterior surface of said anchor body.

19. The suture anchor arrangement of claim 15, wherein said hollow interior opens axially through both said proximal and distal ends.

20. The suture anchor arrangement of claim 15, further including a working suture secured to said interior portion of said loop to interconnect soft tissue to said anchor body when said anchor body is installed within hard tissue.

* * * * *